US008431559B2

(12) United States Patent
Monti

(10) Patent No.: US 8,431,559 B2
(45) Date of Patent: Apr. 30, 2013

(54) TREATMENT OF HOT FLASHES

(75) Inventor: Louis Monti, Mountain View, CA (US)

(73) Assignee: Pherin Pharmaceuticals, Inc., Los Altos, CA (US)

( * ) Notice: Subject to any disclaimer, the term of this patent is extended or adjusted under 35 U.S.C. 154(b) by 0 days.

(21) Appl. No.: 13/288,778

(22) Filed: Nov. 3, 2011

(65) Prior Publication Data
US 2012/0108558 A1 May 3, 2012

Related U.S. Application Data

(63) Continuation of application No. 12/421,421, filed on Apr. 9, 2009, now abandoned.

(60) Provisional application No. 61/123,622, filed on Apr. 9, 2008.

(51) Int. Cl.
A61K 31/58 (2006.01)
A61K 31/33 (2006.01)
A01N 43/00 (2006.01)

(52) U.S. Cl.
USPC .......................................... 514/183; 514/172

(58) Field of Classification Search .................. 514/183, 514/172
See application file for complete search history.

(56) References Cited

U.S. PATENT DOCUMENTS

| | | | |
|---|---|---|---|
| 3,234,093 A | 2/1966 | Wiechert | |
| 5,303,703 A | 4/1994 | Monti-Bloch | |
| 5,563,131 A | 10/1996 | Berliner et al. | |
| 5,792,757 A | 8/1998 | Jennings-White et al. | |
| 5,962,443 A | 10/1999 | Jennings-White et al. | |
| 5,994,333 A | 11/1999 | Jennings-White et al. | |
| 6,057,439 A * | 5/2000 | Jennings-White et al. | ..... 540/24 |
| 6,066,627 A | 5/2000 | Jennings-White et al. | |
| 6,117,860 A | 9/2000 | Jennings-White et al. | |
| 6,140,316 A | 10/2000 | Berliner et al. | |
| 6,165,504 A | 12/2000 | Bell | |
| 6,242,619 B1 | 6/2001 | Jennings-White et al. | |
| 6,331,534 B1 | 12/2001 | Berliner et al. | |
| 6,613,758 B1 | 9/2003 | Bell | |
| 2001/0041699 A1 | 11/2001 | Bell | |
| 2003/0220309 A1 | 11/2003 | Monti et al. | |
| 2004/0209853 A1 | 10/2004 | van der Louw et al. | |
| 2006/0222721 A1 | 10/2006 | Cohen | |
| 2008/0293683 A1 | 11/2008 | Zhu | |
| 2009/0220489 A1 | 9/2009 | Zeller et al. | |

OTHER PUBLICATIONS

Stearns et. al. (Lancet (2002) 360:1851-1861).*
L.B. Barradell et al., on-line abstract of "Cyproterone: A Review of its Pharmacology and Therapeutic Effect in Prostate Cancer", Drugs and Aging, v. 5(1), pp. 59-80, Jul. 1994.
A.C. Eaton et al., abstract of "Cyproterone Acetate in Treatment of Post-orchidectomy Hot Flashes", Lancet, v. 322, iss. 8363, pp. 1336-1337, Dec. 10, 1983.
R.R. Freedman, "Pathophysiology and Treatment of Menopausal Hot Flashes", Seminar in Reproductive Medicine, v. 23(2), pp. 117-125, posted on Medscape Aug. 29, 2005.
R.R. Freedman et al., on-line abstract of "Reduced thermoregulatory null zone in postmenopausal women with hot flashes", American Journal of Obstetrics & Gynecology, v. 181(1), pp. 66-70, Jul. 1999.
D. Grady, "Management of Menopausal Symptoms", New England Journal of Medicine, v. 355, pp. 2338-2347, Nov. 30, 2006.
E. H. Grinnell et al., "Oestrogen Protection Against Acute Digitalis Toxicity in Dogs", Nature, v. 190, No. 4781, pp. 1117-1118, Jun. 17, 1961.
B. I. Grosser et al., "Behavioral and electrophysiological effects of androstadienone, a human pheromone", Psychoneuroendocrinology, v. 25, pp. 289-299, 2000.
L. Monti-Bloch et al., "Effect of putative pheromones on the electrical activity of the human vomeronasal organ and olfactory epithelium", Journal of Steroid Biochemistry and Molecular Biology, v. 39, No. 4B, pp. 593-582, 1991.
L. Monti-Bloch et al., "The Human Vomeronasal System: A Review", Olfaction and Taste XII, Annals of teh New York Academy of Sciences, v. 855, pp. 373-389, Nov. 30, 1998.
I. Savic et al., "Smelling of Odorous Sex Hormone-like Compounds Causes Sex-Differentiated Hypothalamic Activations in Humans". Neuron, v. 31, pp. 661-668, Aug. 31, 2001.
N. Sobel et al., "Blind smell: brain activation induced by an undetected air-borne chemical", Brain, v. 122, pp. 209-217, 1999.
V. Stearns et al., "Hot flushes", Lancet, v. 360, pp. 1851-1861, 2002.
L. J. Stensaas et al., "Ultrastructure of the human vomeronasal organ", Journal of Steroid Biochemistry and Molecular Biology, v. 39, No. 4B, pp. 553-560, 1991.
C.J. Tyrrell, "Controversies in the management of advanced prostate cancer", British Journal of Cancer, v. 79(1), pp. 146-155, 1999.
Wikipedia, Entry on "Dysmenorrhea"http://en.wikipedia.org/wiki/Dysmenorrhea, extracted Nov. 27, 2007.

* cited by examiner

Primary Examiner — Marcos Sznaidman
(74) Attorney, Agent, or Firm — Sam L. Nguyen; Hamilton DeSanctis & Cha, LLP

(57) ABSTRACT

16α,17α-Epoxy-10β-hydroxyestr-4-en-3-one is useful in the treatment of hot flashes by vomeronasal administration.

16 Claims, No Drawings

TREATMENT OF HOT FLASHES

CROSS-REFERENCE TO RELATED APPLICATIONS

This application is a continuation of and claims the benefit under 35 USC 120 of U.S. application Ser. No. 12/421,421, filed 9 Apr. 2009, now abandoned which is incorporated herein by reference. U.S. application Ser. No. 12/421,421 in turn claims the priority under 35 USC 119(e) of U.S. application No. 61/123,622, filed 9 Apr. 2008, which is incorporated into U.S. application Ser. No. 12/421,421 and into this application by reference.

BACKGROUND OF THE INVENTION

1. Field of the Invention

This invention relates to the treatment of hot flashes.

2. Description of the Related Art

Hot flashes

A hot flash is a momentary sensation of heat that may be accompanied by a red, flushed face and sweating. The cause of hot flashes is not known, but may be related to changes in circulation. Hot flashes occur when the blood vessels near the skin's surface dilate to cool. This produces the red, flushed look to the face. A woman may also perspire to cool down the body. In addition, some women experience a rapid heart rate or chills. Hot flashes accompanied with sweating can also occur at night. These are called night sweats and may interfere with sleep. A hot flush is a hot flash plus a visual appearance of redness in the face and neck.

According to Freedman, *Semin. Reprod. Med.*, 2005, 23(2):117-125, hot flashes are the most common symptom of menopause. Although the appearance of hot flashes coincides with estrogen withdrawal, this does not entirely explain the phenomenon because estrogen levels do not differ between symptomatic and asymptomatic women. Luteinizing hormone ("LH") pulses do not produce hot flashes, nor do changes in endogenous opiates. Recent studies suggest that hot flashes are triggered by small elevations in core body temperature ("$T_c$") acting within a reduced thermoneutral zone in symptomatic postmenopausal women. This narrowing may be due to elevated central noradrenergic activation, a contention supported by observations that clonidine and some relaxation procedures ameliorate hot flashes. Because hot flashes are triggered by $T_c$ elevations, procedures to reduce $T_c$, such as lowering ambient temperature, are beneficial. Estrogen ameliorates hot flashes by increasing the $T_c$ sweating threshold, although the underlying mechanism is not known. Recent studies of hot flashes during sleep call into question their role in producing sleep disturbance.

Several health studies have shown that 75% of women surveyed reported having hot flashes in the period between peri- and postmenopause, with duration of symptoms for an average of 4 years. Hot flashes usually last 1 to 5 minutes, with a small percentage persisting for more than 6 minutes. The experience of a hot flash is usually described as sensations of intense heat, sweating, flushing, chills, and clamminess. Sweating is reported most frequently in the face, neck, and chest, but rarely caudally.

Peripheral vasodilation, demonstrated by increased skin temperature and blood flow, occurs during hot flashes in all body areas that have been investigated. Skin temperature increases in the digits, cheek, forehead, upper arm, chest, abdomen, back, calf, and thigh. Blood flow in the finger, hand, calf, and forearm also increases during hot flashes. These changes typically occur within the first few seconds of the reported onset of the hot flash. Sweating and skin conductance (electrical measure of sweating), also increase during hot flashes.

The change in the tone of the autonomic nervous system is responsible for the initiation of hot flashes. Norepinephrine ("NE") released during an increase of the sympathetic tone (or decreased parasympathetic tone) of the autonomic nervous system plays a major role in thermoregulation, acting, in part, through $\alpha_2$-adrenergic receptors. When injected into the preoptic hypothalamus of laboratory animals, NE causes peripheral vasodilation and heat loss, followed by decline in body temperature. Furthermore, gonadal steroids modulate central NE activity. This theory is supported by clinical studies showing that the selective $\alpha_2$-adrenergic agonist clonidine significantly reduces hot flash frequency.

Increased shivering, induced by increased skeletal muscle tone contributes to the production of body heat. The threshold for shivering, measured using the electromyogram of skeletal muscles is lower in symptomatic postmenopausal women than in asymptomatic postmenopausal women. Some relaxation procedures that result in decreased skeletal muscle tone can help decrease hot flashes.

According to Freedman et al., *J. Clin. Endocrinol. Metab.*, 1995, 80:2354-2358, analysis of the circadian rhythm of hot flashes (fit to a 24-hour period sine wave) demonstrated a circadian rhythm (p<0.02) of hot flashes with a peak around 6:30 p.m., lagging the circadian rhythm of $T_c$ in symptomatic women by approximately 3 hours. The majority of hot flashes were preceded by elevations in $T_c$, a statistically significant effect (p<0.05). Hot flashes began at significantly (p<0.02) higher levels of $T_c$ (36.82±0.04° C.) compared with all non-flash periods (36.70±0.005° C.). These data are consistent with the hypothesis that elevated $T_c$ serves as part of the hot flash triggering mechanism.

Since hot flashes occur in most women with the estrogen withdrawal at natural or surgical menopause, there is little doubt that estrogens are involved in their initiation. This is supported by the fact that estrogen administration nearly eliminates hot flashes. However, estrogen withdrawal alone does not explain the etiology of this symptom because there are no correlations between hot flash occurrence and plasma, urinary, or vaginal levels of estrogens, nor are there differences in plasma levels between symptomatic and asymptomatic women. Moreover, clonidine reduces hot flash frequency without changing circulating estrogen levels, and prepubertal girls have low estrogen levels but no hot flashes. Thus, estrogen withdrawal is necessary but not sufficient to explain the occurrence of hot flashes. There is temporal correspondence between pituitary pulsation of LH and temperature changes. However, LH pulses are not the basis for hot flashes.

Therefore, increased sympathoadrenergic tone (or decreased parasympathetic tone), increased body temperature, increased electrodermal activity and increased skeletal muscle tone are conducive to hot flashes in symptomatic menopausal women.

Men may also experience hot flashes when deprived of androgens through castration (loss of both testes by accident or surgery—such as in the treatment of testicular cancer or metastatic prostate cancer) or "chemical castration" (treatment with antiandrogens or luteinizing hormone releasing hormone antagonists—usually in the treatment of metastatic prostate cancer, but occasionally for other medical conditions and in rare instances to voluntarily decrease sexual capability in the treatment of certain sexual offenders).

The Treatment of Hot Flashes

Estrogen replacement therapy. The lowered estrogen levels during menopause are treated by administering 17β-estradiol systemically using oral dosage forms, nasal sprays, and lately low-dose transdermal administration using a patch. However, estrogen replacement therapy is reported to increase the risk for breast cancer, coronary heart disease ("CHD"), thromboembolism, stroke, and dementia when administered with progesterone, and increase the risk of stroke with no reduction of CHD risk when administered alone. In light of the altered risk-benefit ratios for these treatments, they are now being given at lower doses.

Several recent studies report efficacy for certain antidepressants in the treatment of hot flashes. Paroxetine, a selective serotonin-reuptake inhibitor ("SSRI") was shown to decrease hot flash composite scores by 62% (12.5 mg/day) and 65% (25.0 mg/day) in 165 women reporting 2-3 hot flashes/day. The placebo response rate was 37.8%. Fluoxetine is another SSRI used to treat hot flashes. In a study of 81 breast cancer survivors, a crossover analysis showed a reduction in hot flash frequency of ~20% over the placebo condition. Venlafaxine, a serotonin-norepinephrine reuptake inhibitor, has also shown efficacy in treating hot flashes. In a study of 229 women, venlafaxine reduced hot flash scores by 60% from baseline at 75 and 150 mg/day and 37% at 37.5 mg/day compared with 27% for placebo. Side effects of these antidepressants include nausea, dry mouth, somnolence, decreased appetite, and insomnia. Besides the side effects and the slow onset of action, antidepressants require several weeks of sustained administration before achieving therapeutic effects Clonidine ameliorates hot flashes by increasing the $T_c$ sweating threshold. Two small placebo-controlled studies found that oral clonidine reduced hot flash frequency by 46% and transdermal clonidine reduced it by 80%. Two larger studies of breast cancer survivors receiving tamoxifen showed smaller, but significant reductions in hot flash frequency for oral and transdermal clonidine compared with placebo. However, clonidine has a slow onset of action and side effects including hypotension, dry mouth, and sedation.

Gabapentin is an anticonvulsant that binds to the $\alpha_2\delta$ subunit of a voltage-gated calcium channel, which was fortuitously found to ameliorate hot flashes in some patients. A controlled study of 59 women found a reduction of hot flash frequency of 45 vs. 29% for placebo. Side effects of gabapentin include dizziness and peripheral edema.

Nonpharmaceutical treatments include procedures to reduce $T_c$ and ambient temperature, such as dressing in layers and using fans or air conditioning; weight loss; smoking cessation; and relaxation procedures.

Isoflavones or phytoestrogens possess estrogenic properties and are found in soy products and red clover. Black cohosh is another plant-derived substance used to treat hot flashes. A recent review of 22 controlled studies, 12 on soy and 10 on other botanical compounds, found no consistent improvement of hot flashes relative to placebo.

The Vomeronasal Organ and Vomeropherins

The vomeronasal organ ("VNO"; also known as "Jacobson's organ") is a bilateral chemosensory organ found in most vertebrates including humans. In mammals, this organ is accessed through the nostrils (as a pair of blind tubular diverticula found at the inferior margin of the nasal septum), and has been associated with pheromone reception in most species (see generally Muller-Schwarze and Silverstein, "Chemical Signals", Plenum Press, New York (1980); Monti-Bloch et al., *J. Steroid Biochem. Mol. Biol.*, 1991, 39(4):573-582; Monti-Bloch et al., *Ann. NY Acad. Sci.*, 1998, 855:373-389). The axons of the neuroepithelia of the vomeronasal organ, located supra palatinal, form the vomeronasal nerve and have direct input to the hypothalamus and limbic amygdala of the brain. The distal axons of the terminals nerve neurons may also serve as chemosensory receptors in the VNO (Stensaas et al., *J. Steroid Biochem. Mol. Biol.*, 1991, 39(4):553-560). This nerve has direct synaptic connection with the hypothalamus.

Human pheromones delivered to the vomeronasal organ area bind to local receptors and trigger nerve signals that reach the brain inducing physiological and behavioral changes (Grosser et al., *Psychoneuroendocrinology*, 2000, 25:289-299). Synthetic analogs of human pheromones called vomeropherins (defined as substances that bind to receptors in the VNO), can induce robust physiological, pharmacological and behavioral changes when delivered airborne to the VNO. This information is supported by several studies in human volunteers using functional magnetic resonance imaging and positron emission tomography, showing that vomeropherins selectively activate the brain areas (hypothalamus, limbic system, cingulate gyms, anterior thalamus and prefrontal cortex) where their physiological, pharmacological and behavioral effects are integrated. 16α,17α-Epoxy-10β-hydroxyestr-4-en-3-one U.S. Pat. No. 6,057,439, "Steroids as neurochemical stimulators of the VNO to alleviate symptoms of PMS and anxiety", describes the use of a number of steroidal vomeropherins for the treatment of premenstrual dysphoric disorder ("PMDD", also referred to as "premenstrual syndrome" or "PMS") and anxiety by administration to the vomeronasal organ of an individual suffering from those symptoms. 16α,17α-Epoxy-10β-hydroxyestr-4-en-3-one is described in the patent, where it is referred to as 16α,17α-epoxyestr-4-en-10β-ol-3-one. The patent discloses the synthesis of the compound, and claims the compound and pharmaceutical compositions containing it for alleviating the symptoms of PMDD. U.S. Pat. No. 6,331,534, "Steroids as neurochemical stimulators of the VNO to alleviate pain", describes the same steroids for alleviating pain by vomeronasal administration.

The disclosures of the documents referred to in this application are incorporated into this application by reference.

SUMMARY OF THE INVENTION

This invention is the treatment of hot flashes by vomeronasal administration of 16α,17α-epoxy-10β-hydroxyestr-4-en-3-one.

Preferred embodiments of this invention are characterized by the specification and by the features of claims 2 to 16 of this application as filed, and of corresponding pharmaceutical compositions, methods, and uses of these compounds.

DETAILED DESCRIPTION OF THE INVENTION

Definitions

A "Hot flash" or "hot flashes" means the momentary sensation of heat, optionally accompanied by flushing and sweating, also optionally accompanied by tachycardia and chills, seen in perimenopausal and postmenopausal women and castrate men. The term also includes "hot flushes" and "night sweats".

A "perimenopausal woman" is a post-pubertal woman who has experienced partial, but not yet complete, cessation of menses. A "postmenopausal woman" is a post-pubertal woman who has experienced complete cessation of menses. A "menopausal woman" includes both a perimenopausal woman and a postmenopausal woman. The menopause in these women may be either natural (such as with age), surgical (such as by removal of both ovaries), or induced by chemical treatment (such as by treatment with estrogen antagonists, e.g. fulvestrant, raloxifene, tamoxifen, and toremifine).

A "castrate man" is a post-pubertal man who has experienced either actual castration or "chemical castration" (such as by treatment with antiandrogens., e.g. bicalutamide, cyproterone, flutamide, and nilutamide, or luteinizing hormone releasing hormone antagonists, e.g. buserelin, goserelin, leuprolide, and triptorelin).

"Vomeronasal administration" is administration to the human vomeronasal organ. In a clinical setting, this may be accomplished by the use of a probe specifically designed to administer the 16α,17α-epoxy-10β-hydroxyestr-4-en-3-one essentially solely to the vomeronasal organ (such a probe, also designed to measure the effect on vomeronasal tissue, is described in U.S. Pat. No. 5,303,703, "Combined neuroepithelial sample delivery electrode device and methods of using same"). More generally, however, vomeronasal administration comprises intranasal administration in a manner that desirably directs the 16α,17α-epoxy-10β-hydroxyestr-4-en-3-one generally towards the vomeronasal organ.

A "therapeutically effective amount" means the amount of 16α,17α-epoxy-10β-hydroxyestr-4-en-3-one that, when administered to the vomeronasal organ of an individual suffering from hot flashes, is sufficient to effect treatment for the hot flashes. "Treating" or "treatment" of hot flashes includes one or more of:

(1) inhibiting the occurrence of hot flashes,
(2) relieving hot flashes when they occur, and
(3) palliating the symptoms of hot flashes.

16α,17α-Epoxy-10β-hydroxyestr-4-en-3-one and its preparation

16α,17α-Epoxy-10β-hydroxyestr-4-en-3-one is the compound of the formula

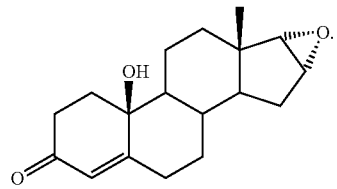

The preparation of 16α,17α-epoxy-10β-hydroxyestr-4-en-3-one is described in U.S. Pat. No. 6,057,439.

A preparation from the readily commercially available steroid estrone is illustrated in the following reaction scheme:

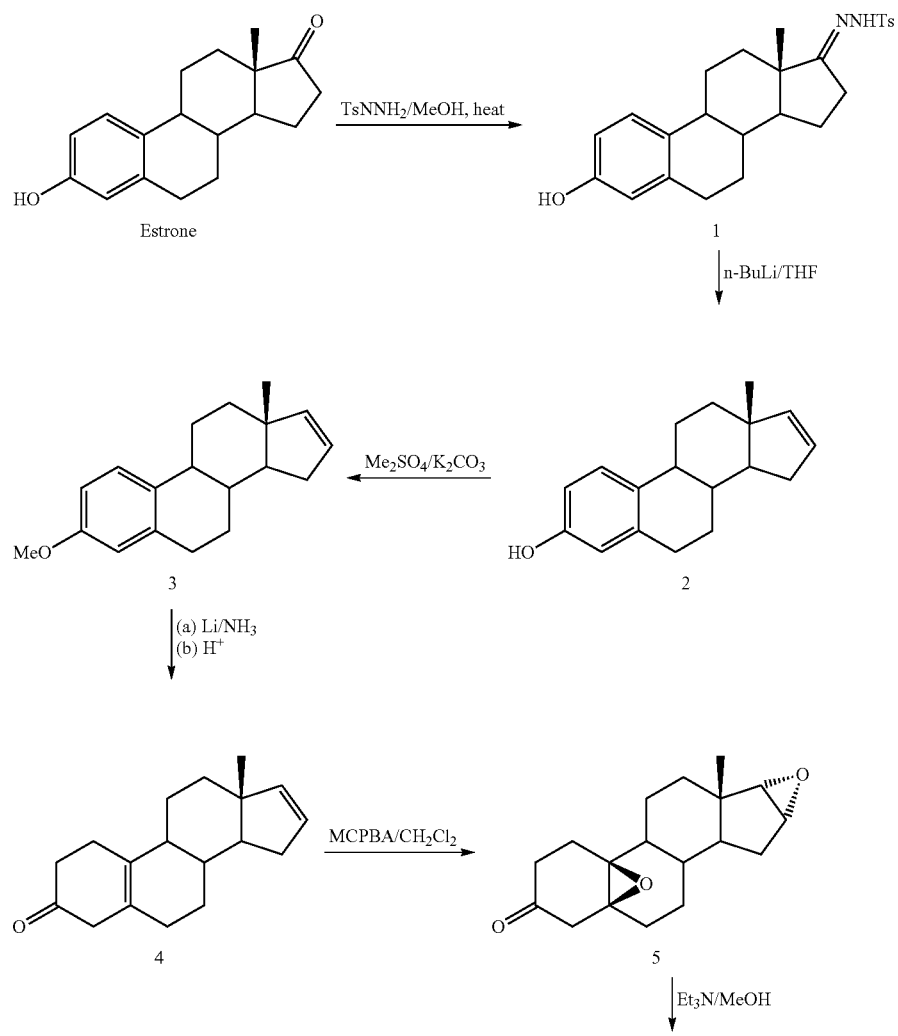

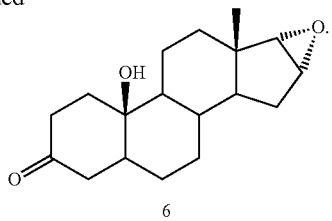

6

In the first step, estrone, an excess of 4-toluenesulfonylhydrazide, and methanol are refluxed under an inert atmosphere with stirring for 24 hours, forming a suspension. This suspension is filtered, and the filtrates concentrated to give 1. In the second step, an excess of a solution of n-butyllithium in hexanes is added to a solution of 1 in anhydrous tetrahydrofuran under argon cooled in an ice bath. The reaction mixture is stirred for 72 hours while gradually warming to room temperature, then ice and saturated aqueous $NH_4Cl$ are added and the aqueous and THF layers separated. The THF layer is dried with $MgSO_4$, filtered, and the solution concentrated under vacuum. The crude product is dissolved in ethyl acetate/hexanes and flash filtered through silica gel, then concentrated under vacuum; then decolorized by dissolution in methanol, treatment with charcoal, and reconcentration. 2 is isolated by addition of water and cooling, then filtered and crystallized from methyl tert-butyl ether.

In the third step, a suspension of 2, an excess of $K_2CO_3$, and acetone are refluxed with stirring and moisture exclusion, an excess of methyl sulfate added, and the reaction mixture stirred for 16 hours. Water is then added and the mixture refrigerated for 72 hours, and the resulting suspension filtered and the residue washed with a mixture of methanol and aqueous NaOH, then with water. The residue is suspended in methanol, decolorized with charcoal, filtered, and the filtrate concentrated, cooled, and filtered to give 3. In the fourth step, anhydrous ammonia is distilled through a KOH tower into a flask fitted with dry ice/acetone condensers and a stirrer. 3, dissolved in isobutanol and anhydrous THF, is added, followed by the slow addition of an excess of lithium wire. The reaction mixture is stirred for 4 hours and the reaction quenched by the addition of methanol, then stirred overnight while the ammonia is allowed to evaporate. Water is then added, and the resulting suspension extracted three times with methyl tert-butyl ether. The organic extract is washed with brine, dried over $MgSO_4$, and filtered, then concentrated under vacuum. The resulting syrup is taken up in acetone and aqueous oxalic acid added and stirred for 8 hours. The hydrolysis mixture is poured into saturated aqueous $NaHCO_3$, and extracted with methyl tert-butyl ether. The organic extract is washed with brine, dried over $Na_2SO_4$, and filtered. The filtrate is concentrated under vacuum and dried over $P_2O_5$ to give 4 as a solid, which is crystallized from hexanes.

In the fifth step, a 2-fold excess of 3-chloroperoxybenzoic acid suspended in $CH_2Cl_2$ is added slowly with stirring to a cooled (ice/salt bath) solution of 4 in $CH_2Cl_2$. The ice/salt bath is removed and the mixture stirred for 5 hours, then the resulting suspension filtered. The filtrate is washed with aqueous $Na_2S_2O_3$, aqueous $NaHCO_3$, and brine, dried over $MgSO_4$, filtered, and concentrated under vacuum, then dried overnight over $P_2O_5$ to give 5 as a solid, which is dissolved in ethanol, decolorized with charcoal, filtered, concentrated, and cooled to yield 5. In the final step, 5 is mostly dissolved in methanol and a 3-fold excess of triethylamine is added, causing dissolution of the remaining solid. The mixture is stirred for 4 hours, then concentrated under vacuum to give a solid residue of 16α,17α-epoxy-10β-hydroxyestr-4-en-3-one, 6. This is dissolved in ethanol, decolorized with charcoal, filtered, concentrated, cooled, filtered, and the residue dried over $P_2O_5$ to give 16α,17α-epoxy-10β-hydroxyestr-4-en-3-one as a fine white crystalline solid.

A person of ordinary skill in the art will have no difficulty, considering that skill and this disclosure (including U.S. Pat. No. 6,057,439), in preparing 16α,17α-epoxy-10β-hydroxyestr-4-en-3-one.

Acute and multidose (28 day) toxicity studies in rats, mice, rabbits and dogs with single (up to 100 μg/rat, 400 μg/rabbit, 600 μg/dog) and repeated (up to 50 μg/rat/day, 300 μg/dog/day) intranasal doses and single (up to 2.5 mg/kg in rats, mice, rabbits) and repeated (up to 2.5 mg/kg/day in rats and rabbits) intravenous doses of 16α,17α-epoxy-10β-hydroxyestr-4-en-3-one demonstrated that the compound was well tolerated in all species tested, with no deaths or adverse clinical signs or effects on laboratory or pathology parameters observed.

Genotoxicity tests revealed no evidence of mutagenic or clastogenic potential of the compound when examined in the Ames reverse mutation assay and the in vivo bone marrow micronucleus test. Reproductive toxicity studies in pregnant rabbits revealed no adverse effects on maternal or litter parameters attributable to the compound at intravenous doses up to 2.5 mg/kg/day administered during the period of organogenesis. Preclinical pharmacokinetic studies with the compound demonstrated very low systemic exposure when the compound was administered by repeated or single escalating intranasal doses up to 100 μg/rat, 400 μg/rabbit, and 600 μg/dog. When given to rats, rabbits, or dogs in single repeated intravenous doses up to 2.5 mg/kg, plasma concentrations of the compound generally were dose-proportional and decreased rapidly.

In a group of 14 women of reproductive age, intranasal administration of a nasal spray containing 500 nanograms of 16α,17α-epoxy-10β-hydroxyestr-4-en-3-one per administration (administration by a Valois intranasal spray pump of 50 μL of an aqueous solution of 10 μg/mL 16α,17α-epoxy-10β-hydroxyestr-4-en-3-one with 2% propylene glycol and 2% ethanol) caused statistically significant decreases in respiratory frequency, electromyographic activity, electrodermal activity (skin conductance), and core body temperature; and statistically significant increases in vagal tone; and a not statistically significant increase in cardiac frequency compared to the vehicle.

In another test also in women of reproductive age, intranasal delivery of a nasal spray containing 1600 nanograms of 16α,17α-epoxy-10β-hydroxyestr-4-en-3-one (one administration per nostril by a Valois intranasal spray pump of 50 μL of an aqueous solution of 16 μg/mL 16α,17α-epoxy-10β-hydroxyestr-4-en-3-one with 2% propylene glycol and 2% ethanol) caused a rapid (0.5 to 4 minute latency) decrease in core body temperature of 1±0.23° C. that persisted for 9±2.5 minutes. It also reduced the tone of the sympathoadrenergic system (as assessed by measuring physiologic sinus arrhythmia) within 5 minutes of administration, and the effect persisted for 15 to 20 minutes.

These effects, including especially the lowering of core body temperature, are predictive of the efficacy of the vomeronasal administration 16α,17α-epoxy-10β-hydroxyestr-4-en-3-one in the treatment of hot flashes.

Formulation and Administration

The 16α,17α-epoxy-10β-hydroxyestr-4-en-3-one may be administered vomeronasally by any route suitable. Routes of administration include, but are not limited to, topical applications (e.g. of a dermal or preferably an intranasal cream or gel), nasal spray, nasal powder spray, and the like. Pharmaceutical formulations generally will be formulations designed to administer the drug across mucosal membranes or transdermal formulations. Suitable formulations for each of these methods of administration may be found, for example, in *Remington: The Science and Practice of Pharmacy*, 20 ed., A. Gennaro, ed., Lippincott Williams & Wilkins, Philadelphia, Pa., U.S.A., 2003. Typical preferred compositions will be aqueous solutions for nasal spray, and will contain 16α,17α-epoxy-10β-hydroxyestr-4-en-3-one and water, and typically will also contain one or more pharmaceutically acceptable excipients. Suitable delivery devices for these formulations are the metered-dose nasal spray pumps in common use for intranasal delivery of steroids for allergies and asthma, and the LHRH antagonist nafarelin for endometriosis. Such pumps are made by a number of manufacturers including Valois. Liquid volumes should be such that the formulation is efficiently delivered without an excess either flowing back into the nasal sinuses or dripping from the nose, and a volume of 50 µL has been found convenient, though greater or lesser volumes will also be satisfactory. Exemplary formulations include those discussed in paragraphs [0041] and [0042] above; and a person of ordinary skill in the art will have no difficulty, considering that skill and this disclosure, in preparing suitable formulations and delivery systems of 16α,17α-epoxy-10β-hydroxyestr-4-en-3-one for vomeronasal administration.

A therapeutically effective amount of 16α,17α-epoxy-10β-hydroxyestr-4-en-3-one, when administered in a nasal spray formulation of the type above, is about 200 to 3000 nanograms per administration, preferably 400 to 1600 nanograms per administration, for example about 800 nanograms per administration. It is expected that not more than a few percent of this dose will actually reach the vomeronasal organ, so therapeutically effective amounts when administered essentially solely to the vomeronasal organ will be perhaps 20-fold lower. These doses, both intranasal and direct vomeronasal, are well below any level that would cause a systemic effect other than those mediated through the vomeronasal organ.

Because of the rapid onset of vomeronasally administered 16α,17α-epoxy-10β-hydroxyestr-4-en-3-one, it is expected that the compound may be administered as needed, for example immediately an individual senses the onset of a hot flash, to relieve and palliate the symptoms of that hot flash. It is also expected that the compound may be administered in a scheduled fashion throughout the day, such as from 2 to 8 times/day, for example from 3 to 5 times/day, such as 4 times/day, to prevent the occurrence of hot flashes. Such scheduled administration may be on a uniform schedule, for example at 8 a.m., noon, 4 p.m., and 8 p.m. (for 4 times/day administration), or on a non-uniform schedule where the frequency of administration is correlated with the circadian rhythm of hot flashes, either in the symptomatic population or of the individual being treated. Thus, for example, administration might be at 9 a.m., 3 p.m., 5 p.m., and 7 p.m. (again for 4 times/day) to maximize the administration at the time when the frequency of occurrence of hot flashes is greatest. Of course, even if scheduled administration is being used, it is possible to administer the compound on an as-needed basis if hot flashes are still experienced.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

I claim:

1. A method of treating a menopausal hot flash in a menopausal woman suffering therefrom, comprising vomeronasal administration to the woman of 16α,17α-epoxy-10β-hydroxyestr-4-en-3-one in an amount effective to cause at least one of inhibiting the occurrence of the hot flash, relieving the hot flash when it occurs, and palliating the symptoms of the hot flash.

2. The method of claim 1, where the woman is a perimenopausal woman.

3. The method of claim 1, where the woman is a postmenopausal woman.

4. The method of claim 1, where the 16α,17α-epoxy-10β-hydroxyestr-4-en3-one is administered on a schedule throughout the day.

5. The method of claim 1, where the 16α,17α-epoxy-10β-hydroxyestr-4-en-3-one is administered at the onset of a hot flash.

6. The method of claim 4, where the schedule is a uniform schedule.

7. The method of claim 4, where the 16α,17α-epoxy-10β-hydroxyestr4-en-3-one is administered from 2 to 8 times per day.

8. The method of claim 7, where the 16α,17α-epoxy-10β-hydroxyestr-4-en3-one is administered from 3 to 5 times per day.

9. The method of claim 8, where the 16α,17α-epoxy-10β-hydroxyestr-4-en3-one is administered 4 times per day.

10. The method of claim 6, where the schedule is a schedule correlated with the population circadian rhythm of hot flashes.

11. The method of claim 4, where the schedule is a schedule correlated with the circadian rhythm of hot flashes for the woman being treated.

12. The method of claim 1, where the 16α,17α-epoxy-10β-hydroxyestr-4-en-3-one is administered in a nasal spray.

13. The method of claim 12, where the nasal spray comprises an aqueous solution of 16α,17α-epoxy-10β-hydroxyestr-4-en-3-one.

14. The method of claim 13, where the 16α,17α-epoxy-10β-hydroxyestr-4-en-3-one content of the nasal spray is 200 to 3000 nanograms per administration.

15. The method of claim 14, where the 16α,17α-epoxy-10β-hydroxyestr-4-en-3-one content of the nasal spray is 400 to 1600 nanograms per administration.

16. The method of claim 13, where the nasal spray comprises an aqueous solution of 16 µg/mL 16α,17α-epoxy-10β-hydroxyestr-4-en-3-one, 2% propylene glycol, and 2% ethanol.

* * * * *